United States Patent [19]

Donovan

[11] Patent Number: 4,523,600

[45] Date of Patent: Jun. 18, 1985

[54] DENTAL FLOSSING PRODUCT

[76] Inventor: Marion Donovan, 850 Park Ave., New York, N.Y. 10021

[21] Appl. No.: 510,271

[22] Filed: Jul. 1, 1983

Related U.S. Application Data

[63] Continuation of Ser. No. 153,907, May 28, 1980, abandoned, which is a continuation-in-part of Ser. No. 92,969, Nov. 9, 1979, abandoned.

[51] Int. Cl.³ .............................................. A61C 15/00
[52] U.S. Cl. .......................................... 132/89; 132/90
[58] Field of Search ....................... 132/89, 90, 91, 93

[56] References Cited

U.S. PATENT DOCUMENTS

| | | | |
|---|---|---|---|
| 1,287,926 | 12/1918 | Ecaubert | 132/92 A |
| 1,570,357 | 1/1926 | Lawrenz | 132/92 R |
| 1,839,486 | 1/1932 | Lawton | 132/93 |
| 2,162,240 | 6/1939 | Boldusoff | 132/91 |
| 2,180,522 | 11/1939 | Henne | 132/91 |
| 2,612,177 | 9/1952 | Footer | 132/93 |
| 3,334,477 | 8/1967 | Morin et al. | 57/22 |
| 3,387,615 | 6/1968 | Mackew | 132/91 |
| 3,860,013 | 1/1975 | Czapor | 132/91 |
| 3,972,174 | 8/1976 | London, Jr. | 57/908 |
| 4,070,815 | 1/1978 | Nogishi | 57/908 |
| 4,215,478 | 8/1980 | Thomas | 132/93 |
| 4,265,258 | 5/1981 | Eaton | 132/93 |
| 4,364,380 | 12/1982 | Lewis | 132/91 |
| 4,440,184 | 4/1984 | Smith | 132/91 |

Primary Examiner—Gregory E. McNeill

[57] ABSTRACT

The disclosure concerns an improved dental hygiene technique for removing plaque from human teeth wherein a loop of multifilament flossing thread is trained about fingers on opposite hands of the user and worked in the spaces between the teeth while maintained taut. The flossing loop may be joint-free and comprise many turns of a single, continuous filament, or it may be made from multifilament thread and have a joint formed by gluing, heat sealing, knotting or air splicing. The last mentioned type of loop may include at least one protruding tail which performs a mopping function during plaque removal.

9 Claims, 11 Drawing Figures

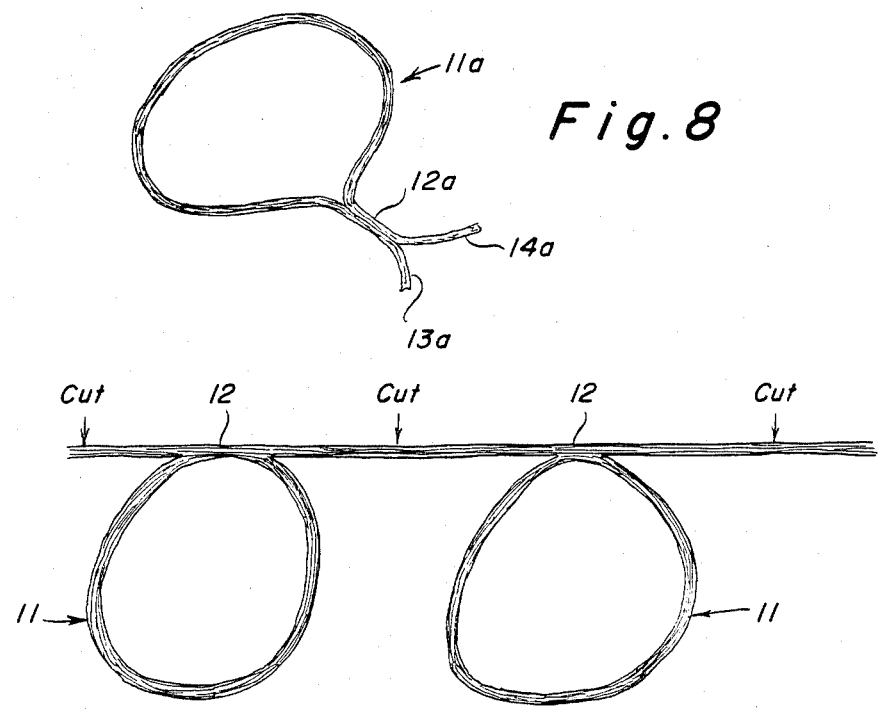
Fig. 8
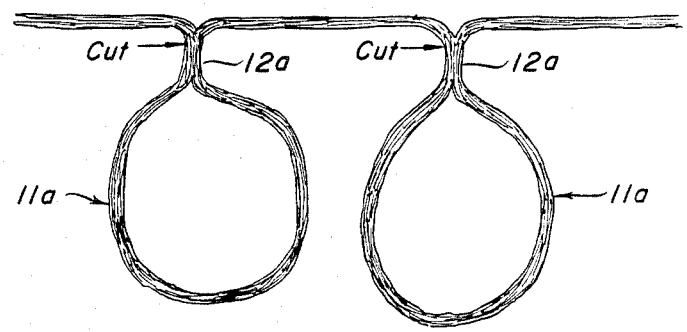
Fig. 9
Fig. 10
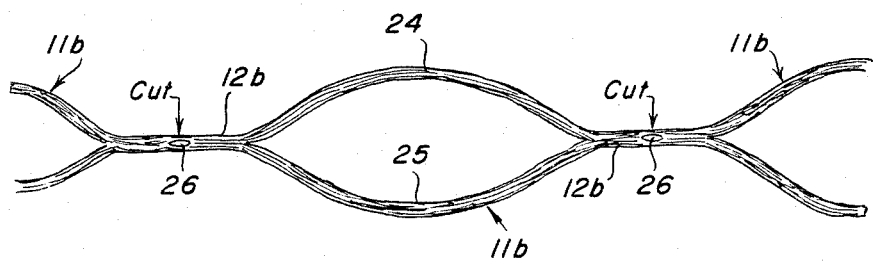
Fig. 11

DENTAL FLOSSING PRODUCT

CROSS-REFERENCE TO RELATED APPLICATION

This application is a continuation of co-pending application, Ser. No. 153,907, filed May 28, 1980, both now abandoned, which was a continuation-in-part of application Ser. No. 92,969, filed Nov. 9, 1979.

BACKGROUND AND SUMMARY OF THE INVENTION

It is generally recognized in the dental profession that plaque which remains on the teeth after brushing is a major cause of tooth and gum problems, and that flossing is the only effective process for removing that plaque. Unfortunately, flossing is not as popular as it should be, particularly among children, probably because of the difficulty and inconvenience of using known flossing products and techniques.

The most common commercial floss product is a multifilament thread of considerable length, e.g., 50 or 100 yards, wound on a packaged spool. Use of this product involves pulling an appropriate section of thread from the package, severing the withdrawn section and wrapping its ends about two fingers on opposite hands, and then working the section in the intertooth spaces while maintaining it in a taut state. These manipulations require a degree of dexterity which makes the flossing process unattractive to many people and very difficult for most children. In addition, maintenance of the tension required for effective plaque removal causes the thread to bind and tend to cut the user's fingers. Moreover, renewal of the active portion of the thread, which becomes frayed as flossing proceeds, necessitates the further inconvenient manipulations of unwinding thread from one finger and winding it onto the other finger. Finally, the packaged spools are somewhat bulky, so carrying the floss in a pocket or in a handbag is a burden. As a result, frequent use of the floss is discouraged.

The prior art also contains various examples of mechanical devices, in the form of frames, which are intended to hold a section of floss under tension, and thereby perform two of the main functions of the user's fingers. While this approach may have superficial appeal, it too has serious disadvantages which have kept flossing in its relatively unattractive condition. In the first place, the addition of another component increases the cost and the bulkiness of the flossing apparatus. Second, the frames of which I am aware are incapable of maintaining the floss under the tension required for good plaque removal throughout the cleaning process, none of them affords a convenient way of renewing the active portion of the thread, and they are not as effective as the fingers for performing the thread-wiggling manipulations which often are needed to insert the floss into small intertooth spaces. Finally, a mechanical frame lacks the sensitive feedback afforded by the user's fingers, and thus makes more likely the infliction of pain as the floss is forced against the gums.

The object of this invention is to provide an improved process and product which make flossing more attractive. According to the invention, the new technique employs a loop of multifilament flossing thread which is trained about the user's fingers. This technique requires only simple manipulations which are well within the capability of even a small child, eliminates binding and cutting of the fingers, and facilitates renewal of the active portion of the thread. Furthermore, since the loop has two potentially active portions intermediate the fingers, the technique inherently is more efficient and more versatile than known practices. For example, both active portions may be worked in the same intertooth space, or those portions may be worked in different spaces to clean either the opposite sides of the same tooth or the corresponding sides of adjacent teeth. In addition, the loop may be trained about a tooth and worked against the inner surface of the tooth. It also should be observed that the thread loop is a compact, unobtrusive element which may be transported easily on the person of the potential user.

The flossing loop may be made by gluing, heat sealing, knotting or air splicing overlapping portions of a multifilament thread. These techniques give an enlarged joint region, which is useful in removing plaque from tooth surfaces which bound a relatively wide intertooth space. They also are capable of providing at least one protruding tail on the loop which acts as a mop which sweeps from the intertooth spaces plaque dislodged from the teeth. A preferred loop is made from two separate lengths of multifilament thread which are air spliced together in longitudinally spaced regions and which are then cut to yield individual loops having diametrically opposed tails. These particular loops are stick-like and stiff enough to make possible packaging in a tube. Another, and perhaps the best, manufacturing technique is a winding process wherein an endless loop is defined by a multiplicity of intertwined turns of a single filament. This technique is considered attractive because it gives a joint-free loop which has the maximum degree of mechanical integrity, and seems to have the potential for achieving high rates of production at low cost. It does not, however, inherently provide loops having the desirable tails and enlarged section which characterize the loops made by the first mentioned techniques.

BRIEF DESCRIPTION OF THE DRAWING

Several embodiments of the invention are described herein with reference to the accompanying drawing, in which:

FIG. 8 is a perspective view of another version of the flossing loop.

FIGS. 9 and 10 are diagrammatic representations of the recommended technique for making the loops shown in FIGS. 1 and 8, respectively.

FIG. 11 is a diagrammatic representation of the preferred technique for making loops from multifilament thread.

DESCRIPTION OF ILLUSTRATED EMBODIMENTS

Figure 1:
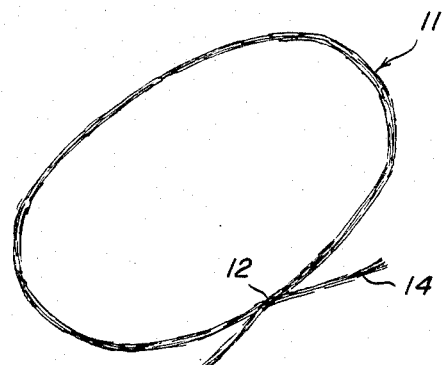
FIG. 1 is a perspective view of one version of the floss loop.

Referring to FIG. 1, one version of the flossing product comprises a loop 11 of multifilament thread having a joint region 12 in which overlapping thread portions are securely connected together. The thread is made of plastic, such as nylon or polyester, and contains 45-65 fine filaments. Any of the multifilament dental floss threads being marketed today may be used in loop 11. It is contemplated that loop 11 be marketed in various sizes, e.g., a 3½" circumference for use by small children, and circumferences of 4½", 6" and 8" for use by older children and adults.

Joint 12, which is about ½" long, may be formed by gluing, heat sealing or knotting. It may also be formed by the air splice technique, wherein the overlapping thread portions are securely connected solely by entanglement or melding of the filaments. These manufacturing techniques necessarily provide tails or tag ends 13 and 14 of thread which project about 1" in opposite directions from joint 12. The tails may be removed. However, since, as pointed out below, the tails perform a useful function during plaque removal, it is recommended that they be retained.

It should be noted that the joints 12 formed by the techniques mentioned above necessarily have cross sections slightly larger than the cross section of the thread itself. As explained later, this enlargement is useful in certain plaque removal procedures.

It is also possible to form the floss loop by a winding process. In this case, the loop is defined by winding a multitude (e.g., 45-65) of turns of a single, fine filament about a mandrel. The turns are intertwined, or twisted, so the thread exhibits a reasonable degree of coherency. If a higher degree of coherence is desired, wax can be incorporated during winding, or a pre-waxed filament may be used. Since the wound loop is endless (i.e., joint-free), it affords the maximum degree of mechanical integrity. In addition, the winding process appears attractive from the manufacturing standpoint because it seems to have the potential for achieving high rates of production at low cost. However, these advantages are offset somewhat by the fact that the process does not inherently provide loops with tails. The loops also lack an enlarged region, but this disadvantage can be eliminated easily merely by adding a patch of adhesive to a localized section of the formed loop.

Figure 2:
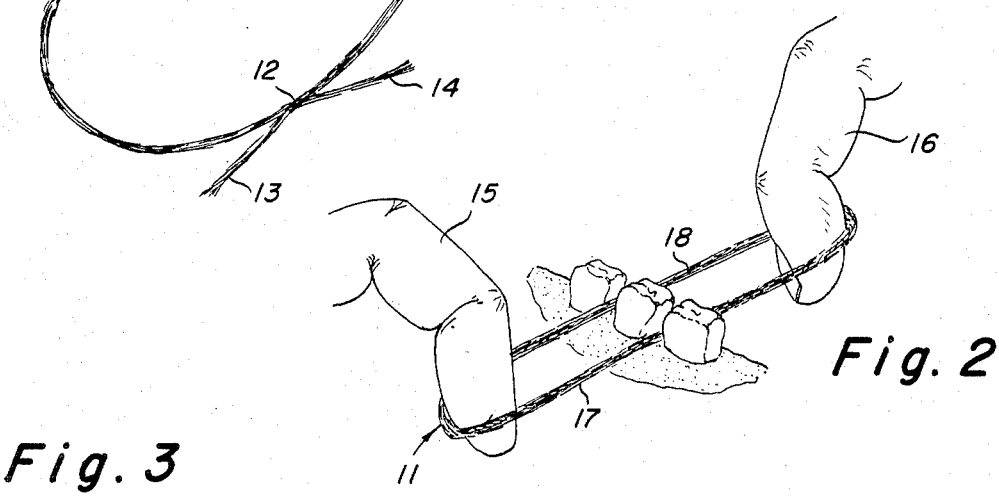
FIG. 2 is a perspective view showing one way in which the loop is trained about the user's fingers during the flossing procedure.
Figure 3:
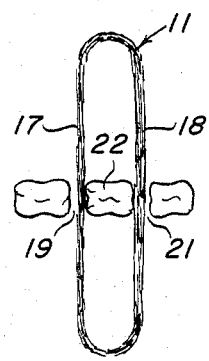
FIGS. 3–7 are diagrammatic plan views of a series of teeth showing various techniques of using the floss loop.
Figure 4:
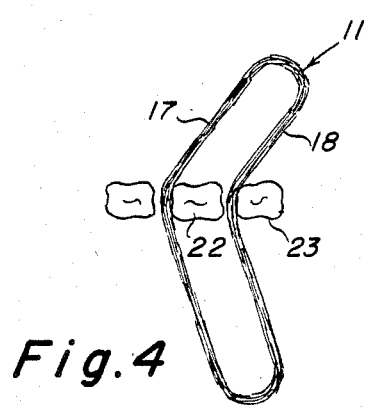
Figure 5:
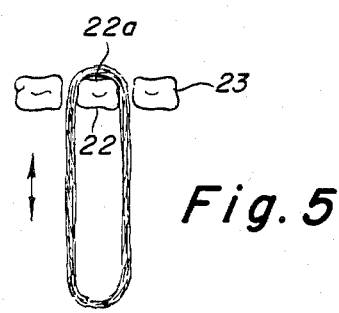
Figure 6:
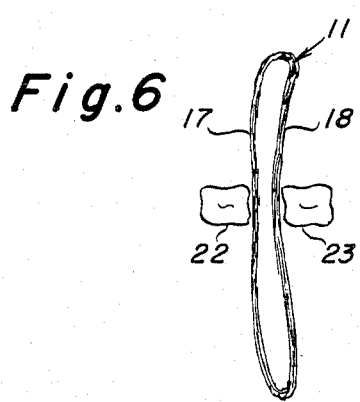

As shown in FIG. 2, the improved plaque removal process involves training loop 11 about fingers 15 and 16, usually the index fingers, on opposite hands of the user, and then working the intermediate loop portions 17 and 18 in the intertooth spaces while maintaining the loop in a taut condition. Various plaque removal procedures may be followed. For example, as indicated in FIG. 3, the intermediate portions 17 and 18 may extend through different intertooth spaces 19 and 21 and be worked up and down against the opposite sides of tooth 22. Alternatively (see FIG. 4), the ends of loop 11 may be pulled sideways to cause portions 17 and 18 to work against corresponding sides of adjacent teeth 22 and 23. After either of these procedures, the finger inside the mouth may be withdrawn to allow loop 11 to become trained about a tooth 22, as shown in FIG. 5. Now, the thread may be worked against the inner surface 22a of the tooth using the fingers of the other hand. If the intertooth space is unusually wide, both intermediate portions 17 and 18 are placed in the same space (see FIG. 6). In this procedure, the two portions 17 and 18 can be worked against the facing side surfaces of adjacent teeth, or they can be worked together against the side surface of one tooth. Placement of both intermediate portions 17 and 18 in the same intertooth space also is advantageous because those strands coact as tweezers which grip, and thereby convey from the intertooth space, plaque dislodged from the teeth.

Since the joint region 12 is enlarged, it too may be used to advantage in wide intertooth spaces. In addition, this enlarged region is an especially useful plaque removal means in any space where the plaque deposit is large or is difficult to dislodge.

It will be understood that flossing should be carried out in each of the intertooth spaces, and that a complete flossing may involve use of one or all of the various loop-manipulating procedures. As flossing proceeds, the active sections of intermediate portions 17 and 18 may become frayed and lose their effectiveness. If so, they can be renewed easily by merely advancing loop 11 lengthwise about fingers 15 and 16 by manipulating it with the remaining fingers.

Figure 7:
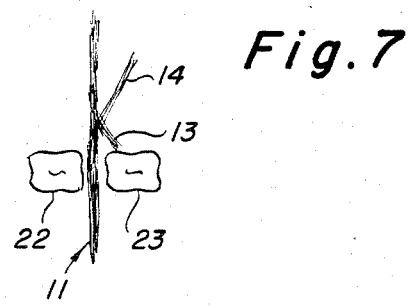

Although, for effective plaque removal, loop 11 must be maintained taut, the tails 13 and 14 remain free and unstressed. Moreover, as indicated in FIG. 7, these tails will be bent backwards as the thread is moved longitudinally in opposite directions through an intertooth space. As a result, the tag ends flop around when they are worked in an intertooth space and act as a mop. This facilitates removal from the space of plaque which has been dislodged from the teeth. The mopping action is quite gentle, so it is an especially desirable way to wipe loose plaque from the gums.

FIG. 8 depicts an alternative flossing loop made from a single length of multifilament thread. Here, the loop 11a is created by joining together overlapping thread portions which, in contrast to the FIG. 1 embodiment, extend in the same direction. The joint 12a may be formed by any of the techniques mentioned earlier. In the case of gluing, heat sealing and air splicing, joint 12a usually will have a length on the order of ½"0 to 1". Therefore, in these cases the joint itself defines a tail which can perform the mopping function, and the free thread ends 13a and 14a which are left after the forming step preferably are cut off. On the other hand, if the overlapping thread portions are joined by knotting, the joint 12a would be too short to be an effective mopping tail. Therefore, when this joining technique is used, it is recommended that the free thread ends 13a and 14a be retained.

It will be observed that when the loop 11a is formed by gluing, heat sealing or air splicing, joint 12a will protrude from the thread circlet, rather than become part of the circlet itself as in the FIG. 1 embodiment. This is an advantage because it affords to the user a greater degree of selectivity as regards use or non-use of the mopping feature.

The loops 11 and 11a of FIGS. 1 and 8, respectively, may be manufactured individually from relatively short lengths of multifilament thread. However, economic considerations indicate that it is better to form the loops at spaced intervals along a continuous, long length of thread, as indicated in FIGS. 9 and 10, and then separate the individual loops from the series after the joints are created.

Another, and I believe the best, way of forming flossing loops from multifilament thread is illustrated in FIG. 11. According to this embodiment, the loops 11b are made from two separate, long lengths 24 and 25 of multifilament thread. These threads are fed side-by-side through an air splicing head which is operated intermittently, and during pauses in thread movement, to join the threads together in longitudinally spaced regions 12b. After splicing, the loops are separated by cutting through each joint intermediate its ends. It has been observed that each splice 12b, which is about 1" long, has a centrally located nodal region 26 of about ⅛" in length wherein the two threads 24 and 25 do not become entangled. This region 26, therefore, marks and defines the appropriate location for each cut.

The loops 11b of FIG. 11 have a pair of diametrically opposed tails defined by the entangled filaments of the bounding splices. Moreover, contrary to the impression given by the simplified showing in FIG. 11, it has been found that the loop-defining threads 24 and 25 actually become twisted together during air splicing. These two features give loop 11b the character of a stick-like product which is stiff enough to make practicable packaging of a set of loops in a small acetate tube. As a result, the preferred loop 11b affords packaging and merchandising advantages not obtainable with its somewhat unruly counterparts 11 and 11a. Loop 11b also is attractive because it includes an extra mopping tail and, as in the case of loop 11a, facilitates selection and exclusion of the mopping function. Finally, it will be noted that the technique of FIG. 11 utilizes all of the thread, and thus wastes nothing.

Although it is preferred that the threads in the FIG. 11 embodiment be joined by air splicing, it should be evident that any of the other joining techniques mentioned herein may be used.

It should be evident that, if desired, the manufacturing techniques represented by FIGS. 9-11 may involve use of multiple loop-forming stations so that a plurality of loops can be made simultaneously.

In cases where joint 12, 12a or 12b is glued, the adhesive itself may serve as an abrasive, or the adhesive may act as a binder for incorporated abrasive particles. Moreover, such an abrasive region, or several such regions, may be used in any of the loops formed by the other manufacturing techniques. The presence of such abrasive regions may be beneficial for those people whose saliva creates a rapid build-up of large plaque deposits. It may also be desirable to incorporate a flavoring substance in the thread loops. This addition would make flossing a more appealing task, and thus tend to encourage its practice, particularly by children.

Although it is believed that unwaxed floss thread is a better plaque removal tool than waxed thread, any of the floss loops of this invention may incorporate wax. In some cases, a prewaxed thread or filament can be used, but in others, for example, loops made by air splicing, the wax must or should be applied after the loop is formed.

I claim:

1. A floss type plaque removal implement comprising a continuous loop of multifiliment thread having at least one joint region wherein overlapping portions of the thread are connected together securely, and at least one tail which is formed as an integral extension of said multifiliment thread from said joint region, the loop being so sized that it may be trained about fingers on opposite hands of the user and extend therebetween in a taut state through interdental spaces.

2. The plaque removal implement of claim 1 wherein the loop is defined by a single length of multifilament thread and has a single joint region from which projects two tails consisting of the free ends of said thread.

3. The plaque removal implement of claim 2 wherein said tails project a length of about one inch.

4. The plaque removal implement of claim 1 wherein the loop is defined by a single length of multifilament thread and has a single joint region defined by the interconnected thread from which projects a single tail consisting of select interconnected thread.

5. The plaque removal implement of claim 4 wherein said tail projects a length of about one inch.

6. The plaque removal implement of claim 1 wherein the loop is defined by separate lengths of multifilament threads which are connected together by two diametrically opposed joint regions defined by the interconnecting threads from which project two tails from each said joint region, said tails each consisting of said interconnected threads.

7. The plaque removal implement of claim 6 wherein said tails project a length of about one inch.

8. The plaque removal implement of claim 1 wherein said overlapping portions are connected together by a connecting means selected from a knot, a heat seal, an adhesive or by mechanical entanglement of the filaments.

9. A floss type dental hygiene product comprising a plurality of implements as defined in claim 1 which are interconnected in a series along the multi-filament thread.

* * * * *